US012582605B2

(12) United States Patent
Nowak et al.

(10) Patent No.: US 12,582,605 B2
(45) Date of Patent: *Mar. 24, 2026

(54) EXTENDED RELEASE FORMULATIONS OF CANNABINOIDS

(71) Applicant: Glatt GmbH, Binzen (DE)

(72) Inventors: Reinhard Nowak, Lörrach (DE); Zafar Iqbal, Sloatsburg, NY (US); Neha Chavan, Jamaica, NY (US)

(73) Assignee: Glatt GmbH, Binzen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/512,967

(22) Filed: Jul. 16, 2019

(65) Prior Publication Data

US 2020/0046787 A1     Feb. 13, 2020

Related U.S. Application Data

(60) Provisional application No. 62/700,107, filed on Jul. 18, 2018.

(51) Int. Cl.
| | |
|---|---|
| *A61K 9/16* | (2006.01) |
| *A61K 9/00* | (2006.01) |
| *A61K 9/48* | (2006.01) |
| *A61K 31/00* | (2006.01) |
| *A61K 31/352* | (2006.01) |
| *A61K 36/185* | (2006.01) |

(52) U.S. Cl.
CPC .......... *A61K 9/1652* (2013.01); *A61K 9/0053* (2013.01); *A61K 9/0056* (2013.01); *A61K 9/1611* (2013.01); *A61K 9/1617* (2013.01); *A61K 9/1623* (2013.01); *A61K 9/1635* (2013.01); *A61K 9/1658* (2013.01); *A61K 9/1664* (2013.01); *A61K 9/1676* (2013.01); *A61K 9/48* (2013.01); *A61K 31/352* (2013.01); *A61K 31/658* (2023.05); *A61K 36/3482* (2024.05)

(58) Field of Classification Search
CPC .................................................. A61K 9/4891
See application file for complete search history.

(56) References Cited

U.S. PATENT DOCUMENTS

| | | | |
|---|---|---|---|
| 5,662,932 | A | 9/1997 | Amselem et al. |
| 5,891,496 | A | 4/1999 | Hannah et al. |
| 6,328,992 | B1 | 12/2001 | Brooke et al. |
| 6,354,728 | B1 | 3/2002 | Bretschneider et al. |
| 6,380,175 | B1 | 4/2002 | Hussain et al. |
| 6,383,513 | B1 | 5/2002 | Watts et al. |
| 6,509,005 | B1 | 1/2003 | Peart et al. |
| 6,713,048 | B2 | 3/2004 | Peart et al. |
| 6,946,150 | B2 | 9/2005 | Whittle |
| 7,993,595 | B2 | 8/2011 | Jacob et al. |
| 8,597,685 | B2 | 12/2013 | Jacob et al. |
| 10,179,109 | B2 | 1/2019 | Bosse et al. |

| | | | | |
|---|---|---|---|---|
| 2012/0231083 | A1* | 9/2012 | Carley | ................. A61K 9/2077 |
| | | | | 424/494 |
| 2016/0022627 | A2 | 1/2016 | Smith | |
| 2016/0051480 | A1 | 2/2016 | Taha | |
| 2016/0235673 | A1* | 8/2016 | Preisig | .............. A61K 31/4164 |
| 2018/0085308 | A1 | 3/2018 | Renwick et al. | |
| 2018/0214412 | A1 | 8/2018 | Renwick et al. | |
| 2018/0264013 | A1 | 9/2018 | Dill | |
| 2018/0325861 | A1* | 11/2018 | Domb | ................. A61K 31/352 |
| 2019/0254302 | A1* | 8/2019 | Abbaspourrad | ... A23C 19/0925 |
| 2020/0046643 | A1* | 2/2020 | Nowak | ................. A61K 31/05 |
| 2020/0094955 | A1* | 3/2020 | Selfridge | ............. B64C 39/022 |

FOREIGN PATENT DOCUMENTS

| | | |
|---|---|---|
| CN | 1886117 | 12/2006 |
| EP | 1125629 | 8/2001 |
| EP | 1325775 | 7/2003 |
| EP | 1361864 | 12/2013 |
| WO | WO 2002/064109 | 9/2002 |
| WO | WO 04052607 | 6/2004 |
| WO | WO 2008/027442 | 3/2008 |
| WO | WO 2016/144376 | 9/2016 |
| WO | WO 2016/205923 | 12/2016 |
| WO | WO 2017/072762 | 5/2017 |
| WO | WO 2018/035030 | 2/2018 |
| WO | WO 2018/071581 | 4/2018 |
| WO | WO 2019/159174 | 8/2019 |

OTHER PUBLICATIONS

The Specialty Excipient: Neusilin, Fuji Chemicals Industries, Sep. 2015. (Year: 2015).*
International Search Report for Application No. PCT/IB2019/000840 dated Jan. 3, 2020.
Written Opinion of the International Search Authority for Application No. PCT/IB2019/000840 dated Jan. 3, 2020.
Written Opinion of the International Search Authority for Application No. PCT/IB2019/000847 dated Jan. 20, 2020.
International Search Report for Application No. PCT/IB2019/000847 dated Jan. 20, 2020.
Written Opinion of the International Search Authority for Application No. PCT/IB2019/0000857 dated Jan. 21, 2020.
International Search Report for Application No. PCT/IB2019/000857dated Jan. 21, 2020.

(Continued)

*Primary Examiner* — Gina C Justice

(74) *Attorney, Agent, or Firm* — Jon E. Gordon; Haug Partners LLP

(57)     ABSTRACT

Compositions for the extended release of one or more cannabinoids, in which the compositions comprise a population of particles. Each particle may comprise the one or more cannabinoids, one or more drug-releasing agents, one or more surfactants, and a core. The core may comprise a porous bead. The one or more cannabinoids may comprise Δ9-tetrahydrocannabinol, cannabidiol, or a combination thereof.

22 Claims, 9 Drawing Sheets

(56) References Cited

Written Opinion of the International Search Authority for Application No. PCT/IB2019/000860 dated Jan. 20, 2020.

International Search Report for Application No. PCT/IB2019/000860 dated Jan. 20, 2020.

U.S. Non-Final Office Action issued for corresponding U.S. Appl. No. 16/513,068 dated May 14, 2020.

Parker, W, 2009, Alcohol-containing pharmaceuticals, The American Journal of Drug and Alcohol Abuse, vol. 9, 195-209; screenshot from https ://pubmed.ncbi.nlm.nih.gov/7171081 / (Year: 2009).

U.S. Non-Final Office Action issued for corresponding U.S. Appl. No. 16/513,154 dated May 19, 2021.

Mydayis, "How Mydayis works", 2020, screenshot of https://www.mydayis.com/adhd-treatment/how-it-works (Year: 2020).

Non-Final Office Action for corresponding U.S. Appl. No. 16/513,068 dated Nov. 9, 2021.

U.S. Non-Final Office Action issued for corresponding U.S. Appl. No. 16/513,068 dated Oct. 8, 2020.

\* cited by examiner

EXTENDED RELEASE FORMULATIONS OF CANNABINOIDS

CROSS-REFERENCE TO RELATED APPLICATIONS

This application claims the benefit of U.S. Provisional Application Ser. No. 62/700,107 filed on Jul. 18, 2018, the entirety of which is herein incorporated by reference.

FIELD OF INVENTION

The present invention relates to an extended release, multiparticulate drug delivery platform for the oral administration of one or more cannabinoids. The drug delivery system of the present invention achieves a targeted pharmacokinetic profile and provides a uniform drug distribution in the gastrointestinal tract. The delivery system of the present invention can be administered as capsules, tablets, sprinkles, or a stick pack for convenience in administration and handling.

BACKGROUND OF THE INVENTION

Cannabis, the plant genus that includes both hemp and marijuana, possesses many medicinal and psychoactive properties that reportedly alleviate a wide range of symptoms experienced in connection with serious medical conditions, while providing safer and fewer serious side effects than most current prescription drugs. For example, cannabis has been used to combat symptoms associated with cancer, anorexia, AIDS, chronic pain, muscle spasticity, glaucoma, arthritis, migraine, and many other illnesses.

Cannabinoids are a class of diverse chemical compounds originating from the cannabis plant that act on cannabinoid receptors, which repress neurotransmitter release in the brain. Δ9-tetrahydrocannabinol (THC) and cannabidiol (CBD) are the two most prominent cannabinoids found in Cannabis. While there are over 100 different cannabinoids so far identified in Cannabis by scientists, CBD and THC are by far the most extensively studied and best understood. CBD and THC both interact with the body's endocannabinoid system, a vital signaling system responsible for regulating a wide array of functions.

THC is a psychotropic chemical derived from marijuana that acts on the body's cannabinoid receptors and resembles chemicals naturally produced by the body. THC is a psychoactive that activates the CB1 and CB2 receptors and affects perception, mood, consciousness, cognition, and behavior. In medicinal application, THC has the properties of an analgesic and an appetite stimulant. THC has also been reported to create a state of relaxation and well-being, induce sleep, and cause a state of euphoria. These effects have been used to treat a variety of health issues, such as pain, inflammation, nausea, sleep apnea, and stress disorders. Additionally, THC has been shown to fight the side effects and symptoms of chemotherapy, multiple sclerosis, glaucoma, AIDS, and spinal injuries.

Currently, there are only three drug products approved by the Food and Drug Administration (FDA) for THC: Marinol®, Syndros®, and Cesamet®. Marinol® and Syndros® both contain dronabinol, a synthetic THC that is insoluble in water and has a pKA of 10.6. Marinol® is available as soft gelatin capsules in dosage strengths of 2.5 mg, 5 mg, and 10 mg, and Syndros® is available as an oral solution (5 mg/ml). Both Marinol® and Syndros® are indicated for the treatment of anorexia associated with weight loss in patients with AIDS and for the treatment of nausea and vomiting associated with cancer chemotherapy in patients who have failed to respond adequately to conventional antiemetic treatments.

Cesamet® contains nabilone, a synthetic cannabinoid that is chemically similar to THC. As a raw material, nabilone is a white to off-white polymorphic crystalline powder. In aqueous media, the solubility of nabilone is less than 0.5 mg/L, with pH values ranging from 1.2 to 7.0. Cesamet® is available as a powder-filled capsule (1 mg/capsule) for oral administration and is indicated for the treatment of the nausea and vomiting associated with cancer chemotherapy in patients who have failed to respond adequately to conventional antiemetic treatments. However, the effects of Cesamet® have been reported to persist for a variable and unpredictable period of time following its oral administration; for example, adverse psychiatric reactions from using Cesamet® can persist for 48 to 72 hours following cessation of treatment.

THC has a duration of action lasting up to 2-4 hours, a psychoactive action lasting 4-6 hours, and an appetite-increasing action that may last up to 24 hours after oral administration. Due to this short duration of action, THC products administered orally have poor or partial response, requiring a patient to rely on multiple daily dosing regimen. Marinol®'s maximum recommended dosage is 15 mg/m$^2$ per dose for 4 to 6 doses per day, and Syndros® has a recommended maximum dosage of 12.6 mg/m$^2$ per dose for 4 to 6 doses per day. Cesamet®'s maximum recommended daily dose is 6 mg given in divided doses 3 times a day.

CBD is another potent chemical derived from marijuana that is widely inhaled by patients from smoking the hemp leaves. To date, the FDA has only approved Epidiolex®, an oral solution (100 mg/ml) containing plant-derived CBD for the treatment of seizures associated with two rare and severe forms of epilepsy, Lennox-Gastaut syndrome and Dravet syndrome, in patients two years of age and older. CBD is a white to pale yellow crystalline solid. It is insoluble in water and is soluble in organic solvents. The primary medical applications of CBD are to combat severe and chronic pain, stress, depression, anxiety, cancer, epilepsy, schizophrenia, multiple sclerosis, migraine, arthritis, and the adverse effects of chemotherapy. Epidiolex® has a maximum recommended maintenance dosage of 10 mg/kg twice daily.

As described above, these FDA-approved drugs are all for multiple-dose administration. Thus, there remains a need in the art for an extended release drug containing one or more cannabinoids. Extended release drug formulations may be useful to reduce the frequency of drug administration, improve patient compliance, reduce drug toxicity (local or systematic associated with high-peak exposure), reduce drug level fluctuation in the blood, stabilize medical conditions with more uniform drug levels, reduce drug accumulation with chronic therapy, improve bioavailability of some drugs because of spatial control, and reduce total drug usage when compared with some immediate release drugs.

Further benefit would be achieved if an extended release drug profile can be applied to a drug combination of THC and CBD. All of the FDA-approved drugs contain either synthetic THC or CBD, not a combination of both. While there are no FDA-approved drugs that use THC and CBD in combination, Sativex® is an oromucosal spray of a formulated extract of the *Cannabis sativa* plant that contains the principal cannabinoids THC and CBD as well as specific minor cannabinoids and other non-cannabinoid components. Sativex® is indicated for the treatment of adult patients with moderate to severe spasticity due to multiple sclerosis (MS) who have not responded adequately to other anti-spasticity medication and who demonstrate clinically significant improvement in spasticity-related symptoms during an initial trial of therapy. Sativex® is available by prescription in Europe, Canada, New Zealand, and Israel. However, Sativex® also requires multi-dose administration—up to a maximum of 12 sprays per day with a minimum 15 minutes between sprays.

The presence of CBD can balance the agonistic activity of THC. THC activates the cannabinoid receptors CB1 and CB2 that are present in the brain and that are responsible for THC's psychoactive effects, while CBD suppresses the CB1 and CB2 receptors by operating as an indirect antagonist of cannabinoid agonists. Hence, CBD suppresses the activation of the CB1 and CB2 receptors by a cannabinoid like THC, creating a balanced effect.

When used in combination, THC and CBD have anti-inflammatory, appetite stimulant, antiemetic, anticonvulsant, antioxidant, neuroprotective, and antitumoral actions. THC and CBD also can be used to combat epilepsy, depression, anxiety, schizophrenia, multiple sclerosis, migraine, and arthritis; and to alleviate the symptoms of cancer, AIDS, and spinal injuries; all of which improves quality of life for patients suffering from those debilitating conditions.

Further, THC and CBD are advantageous over other current prescription medications because they are non-habit forming, safe, and well-tolerated. Currently, about 2 million Americans have become dependent on or abused prescription pain pills because of the habit-forming nature of opioids. Additionally, opioids are associated with higher risk of overdose leading to death. There is a need in the art for a strong non-habit-forming painkiller as well as a well-tolerated and safe pain medication to prevent death from overdosing. Both THC and CBD are non-habit-forming strong painkillers that can replace opioids in treating severe and chronic pain.

In addition, the most prevalent mode of administration of medical cannabis is by smoking. Unfortunately, this mode of administration has adverse effects on the lungs. Cannabis smoke carries more tar and other particulate matter than tobacco, and may be a cause of lung diseases including lung cancer. Smoking may also negatively impact cannabinoids absorption. Studies show that the length of inhalation, hold time, and time between puffs attributed large inter-subject differences in plasma THC concentrations due to differences in the depth of inhalation, as participants titrated their THC dose. Moreover, many patients may find the act of smoking unappealing, as well as generally unhealthy. Accordingly, there is a significant interest in developing other means to administer cannabis to patients.

Thus, there remains a unmet need in the art for an extended release dosage form of THC and CBD, either individually or combined, for the treatment of multiple clinical conditions. A multiparticulate, extended release dosage form as described below would allow for precise dosing, uniform drug delivery, targeted pharmacokinetics, and convenience in administration, all of which are currently unavailable.

SUMMARY OF THE INVENTION

The present invention provides multiparticulate solid oral dosage forms comprising one or more cannabinoids. These dosage forms can be administered as capsules, tablets (regular tablets, orally-disintegrating tablets (ODT), self-disintegrated tablets, chewable tablets), sachets, sprinkles, or stick pack to the recipients, providing an ease in administration and handling. The system may comprise particles (e.g., granules, particle agglomerates of any shape, beads, or pellets) having a size that may range from about 30 μm to about 1500 μm, or about 50 μm to about 1000 μm, in diameter, and with uniform loading. The multiparticulate solid oral dosage forms of the present invention may be formulated in a manner to provide an extended release profile of up to 24 hours, thus providing a once-daily dose regimen that can help achieve higher patient compliance. The dosage forms of the present invention also may be formulated to achieve a targeted pharmacokinetic profile and to provide uniform distribution in the gastrointestinal tract.

One aspect of the current invention relates to a composition for the extended release of one or more cannabinoids. In some embodiments, the composition may comprise a population of particles, wherein each particle comprises: one or more cannabinoids, one or more drug-releasing agents, and a core. In some embodiments, the particles may comprise one or more cannabinoids, one or more drug-releasing agents, a core, one or more solubilizers, and one or more surfactants. The composition may release the one or more cannabinoids over a period of at least 6 hours or over a period of about 12-24 hours. The one or more cannabinoids may be present in the composition in an amount of about 1% to about 90% w/w, or about 5% to about 50%.

In some embodiments, the one or more cannabinoids may comprise THC, CBD, or a combination thereof.

In some embodiments, the one or more drug-releasing agents may comprise one or more gel-forming agents. The one or more gel-forming agents may be selected from glyceryl monooleate, glycerol monostearate, soybean oil, propylene glycol monopalmitostearate, cellulose-based gelling agents, carboxypolymethylenes, hydroxypropyl cellulose, hydroxypropylmethyl cellulose, carboxymethyl cellulose, chitosan, natural gums such as acacia, alginates, carrageen, guar gum, or a combination thereof.

In some embodiments, the ratio of the one or more gel-forming agents to the one or more surfactants may be about 10:1 to about 1:10, or about 8:1 to about 1:8, or about 5:1 to about 1:5, by weight.

In some embodiments, the one or more solubilizers may comprise an oil, glyceride, an alcohol, or a combination thereof. The oil may be selected from oils that include, but are not limited to, cannabis oil and sesame oil.

In some embodiments, the core may comprise a porous bead such as a mesoporous silica bead or a porous biodegradable glass bead. The ratio of pore volume to particle size may range from about 0.001 to about 0.8. In some embodiments, the pores may contain the one or more cannabinoids and the one or more drug-releasing agents. In certain embodiments, the pores may contain the one or more cannabinoids, the one or more solubilizers, the one or more surfactants, and the one or more drug-releasing agents.

In yet further embodiments, the composition for extended release of one or more cannabinoids may comprise a population of particles, wherein each particle comprises: about 1% to about 20% w/w of the one or more cannabinoids, about 5% to about 15% w/w of one or more solubilizers, about 15% to about 35% w/w of one or more drug-releasing agents, about 20% to about 45% w/w of a core, and about 15% to about 35% w/w of one or more surfactants. The composition may release the one or more cannabinoids over a period of at least 6 hours.

In another aspect of the present invention, any of the embodiments of the composition for extended release of one or more cannabinoids may be used in a method of treating a health issue in a subject in need thereof, wherein the health issue is selected from the group consisting of pain, nausea, sleep apnea, stress disorders, inflammation, depression, anxiety, epilepsy, schizophrenia, migraines, arthritis, weight loss, poor appetite, and a combination thereof. In some embodiments, the composition may be administered orally. In certain embodiments, prior to administration, the composition may be sprinkled on food or nutrient that is solid, semi-solid, or liquid; into water; or into other types of liquid drink.

BRIEF DESCRIPTION OF THE DRAWINGS

For a better understanding of the present invention, reference is made to the following description of an exemplary embodiment thereof, and the accompanying drawing, wherein.

DETAILED DESCRIPTION

Figure 1A:
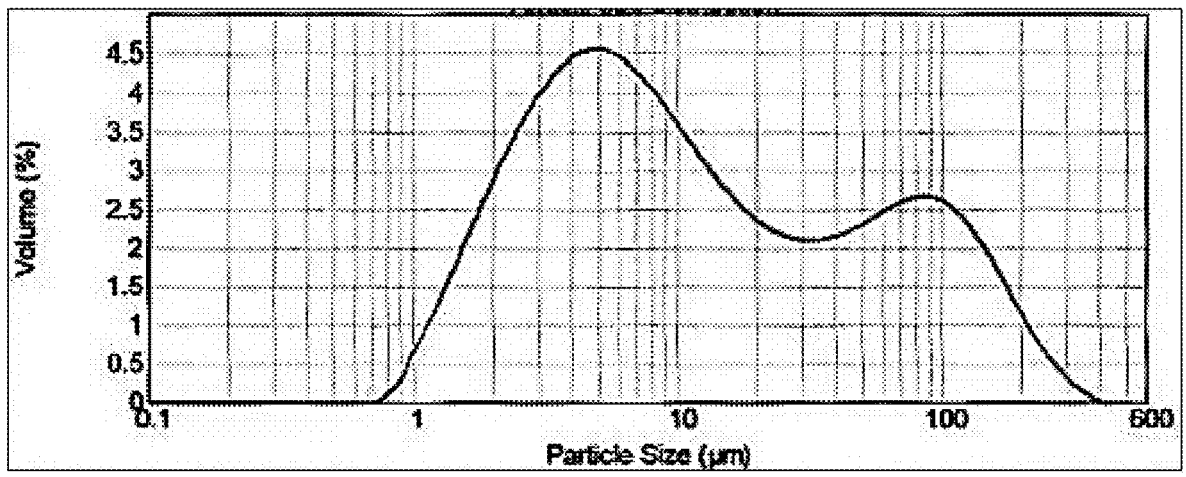
FIGS. 1A and 1B shows particle size distribution using dynamic light scattering technique (Malvern Instruments, USA) for: plain Neusilin US2 beads (FIG. 1A) and Neusilin US2 beads loaded with probucol in sesame oil and surfactant (FIG. 1B).

According to the present invention, multiparticulate, extended release dosage forms are provided for administering one or more cannabinoids. In one aspect, the one or more cannabinoids comprise THC, CBD, or a combination thereof. In some embodiments, the one or more cannabinoids may be in an amount of about 1% to about 90% w/w, or about 5% to about 50%. In certain embodiments, a final composition of THC and CBD, either individually or together, may range from about 1% to about 90% w/w.

In embodiments of the invention, the compositions may comprise a population of particles, in which each particle comprises: one or more cannabinoids, one or more drug-releasing agents, and a core. In some embodiments, the compositions may comprise a population of particles, in which each particle comprises: one or more cannabinoids, one or more drug-releasing agents, one or more solubilizers, one or more surfactants, and a core. In certain embodiments, the ratio by weight of [the one or more cannabinoids+the one or more drug–releasing agents+the one or more solubilizers+the one or more surfactants] to the core may be about 5:1 to about 1:5, or about 3:1 to about 1:3, or about 2:1 to about 1:1. In another aspect, over about 50% of the particles may be between about 30 μm and about 2000 μm, or between about 50 μm and about 1000 μm, in diameter. In yet another aspect, the particles may be provided in a capsule, tablet, or sachet.

In an aspect of the invention, the embodiments of the varying compositions of the present invention may be used in a method of treating a health issue in a subject in need thereof, wherein the health issue is selected from the group consisting of pain, nausea, sleep apnea, stress disorders, inflammation, depression, anxiety, epilepsy, schizophrenia, migraines, arthritis, weight loss, poor appetite, and a combination thereof. In one embodiment, the composition may be administered orally. In another embodiment, prior to administration, the composition may be sprinkled on food or nutrient that is solid, semi-solid, or liquid; into water; or into other types of liquid drink.

In some embodiments, the one or more cannabinoids is solubilized in sesame oil and loaded onto mesoporous silica beads. The drug is loaded in the pores of the beads by the capillary action. In some embodiments, the drug is loaded in the pores of the beads followed by a surfactant and a gel-forming lipid excipient to control the drug release.

Compositions of the Present Invention

As used herein, the term "extended release" is characterized by the gradual release of the one or more cannabinoids from the particles of the composition over an extended period of time, optionally greater than about 30 minutes. With extended release, the rate of release of the one or more cannabinoids from the particles is controlled in order to maintain therapeutic activity of the one or more cannabinoids for a longer period of time. In some embodiments of the current invention, the composition may release greater than about 40% of the one or more cannabinoids over a period of about 6 hours or more. In certain embodiments, the composition may release the one or more cannabinoids over a period of about 12 hours to about 24 hours.

As used herein, the term "solubilizer" refers to a solubility enhancement excipient that increases the bioavailability of cannabinoids. The purpose of the one or more solubilizers is to achieve a concentrated, homogenous, and stable solution in order to deliver the cannabinoids in an efficient way. The one or more solubilizers for use in the present invention may include, but are not limited to, oil, glyceride, an alcohol, or a combination thereof. The oil may be selected from the group consisting of cannabis oil, borage oil, coconut oil, cottonseed oil, soybean oil, safflower oil, sunflower oil, castor oil, corn oil, olive oil, palm oil, peanut oil, almond oil, sesame oil, rapeseed oil, peppermint oil, poppy seed oil, canola oil, palm kernel oil, hydrogenated soybean oil, hydrogenated vegetable oil, and a combination thereof. The glyceride may be selected from the group consisting of a monoglyceride, diglyceride, triglyceride, and a combination thereof. The alcohol may be a monohydric alcohol, e.g., ethanol, methanol, or isopropyl alcohol. In some embodiments, the one or more solubilizers may be a hydroalcoholic mixture.

As used herein, the term "drug-releasing agents" relates to agents that control drug delivery so that the cannabinoids are released in a predesigned manner. As a result, the drug-releasing agents contribute to the rate and extent of the cannabinoids' active availability to the body.

In one aspect, the one or more drug-releasing agents may comprise one or more lipid-based gel-forming agents. The gel-forming agent may be added to form a viscous liquid crystalline phase that can control the release of the drug from the composition. Gel-forming agents extend the release of drug by forming differing viscosities of the gel barrier between the source and surrounding medium, which can be optimized by adjusting the amount of gel-forming agent present in the composition, and/or, in some embodiments, by adjusting the amount of gel-forming agent with respect to the amount of a surfactant in the composition.

The one or more gel-forming agents may be selected from glyceryl monooleate (e.g., Capmul GMO-50; Abitec Corp., USA), glycerol monostearate (e.g., Geleol™ Mono and Diglycerides; Gattefosse, USA), glyceryl distearate, polyglyceryl-3 dioleate (Geloil®); Gattefosse, USA), soybean oil, propylene glycol monopalmitostearate (e.g., Monosteol™; Gattefosse, USA), cellulose-based gelling agents, carboxypolymethylenes (e.g., Carbopol® or Carbomer®), hydroxypropyl cellulose, hydroxypropylmethyl cellulose, carboxymethyl cellulose, chitosan, natural gums (e.g., acacia, alginates, carrageen, guar gum), and a combination thereof. In certain embodiments, the one or more gel-forming agents may comprise glycerol monooleate.

In embodiments in which the composition comprises one or more gel-forming agents and one or more surfactants, the weight ratio of the one or more gel-forming agents to the one or more surfactants may be about 10:1 to about 1:10, or about 8:1 to about 1:8, or about 5:1 to about 1:5. According to certain embodiments, the weight ratio of the one or more gel-forming agents to the one or more surfactants may be about 1:1. In certain embodiments, cellulose-based and gum-based gelling agents can be added with or without surfactants.

As used herein, the term "core" can refer to a carrier onto which the one or more cannabinoids, the one or more drug-releasing agents, etc., can be loaded, and from which these components can be released. In embodiments of the current invention, the core may comprise a silica bead, a biodegradable glass bead, or any other bead made of any compatible materials known in the art as suitable for oral administration (e.g., porous ceramics, porous calcium carbonate particles, porous zeolite particles, etc.)

The core may also comprise one or more pores that extend from the surface of the core. The core may contain the one or more cannabinoids and the one or more drug-releasing-agents, and, in some embodiments, one or more solubilizers and/or one or more surfactants. According to some embodiments, the ratio of pore volume to particle size of the core may be between about 0.001 to about 0.8. Within that range, the pores may be configured such that the one or more drug-releasing agents are located in the pores closer to the surface of the core than the one or more cannabinoids. In embodiments wherein one or more solubilizers and one or more surfactants are in the composition, the pores may be configured such that the one or more drug-releasing agents are located in the pores closer to the surface of the core than the one or more cannabinoids, the one or more solubilizers, and the one or more surfactants.

According to the present invention, the core is selected in consideration of loading capacity and its capability of achieving a free-flowing multiparticulate system. According to some embodiments, the core comprises mesoporous silica (e.g. Syloid® XDP 3150 (Grace, USA), Davisil® LC150A (Grace, USA), Neusilin® US2 (Fuji Chemicals, Japan)). Particle size, pore volume and specific surface area for the silica beads are given in Table 1 below.

TABLE 1

| Physical properties of silica beads | | | |
| --- | --- | --- | --- |
| Physical properties | Syloid ® XDP 3150 | Davisil ® LC150A | Neusilin ® US2 |
| Particle Size Distribution (µm) | 120-170 | 315-500 | 44-177 |
| Specific Surface Area (m²/g) | 320 | 340 | 300 |
| Pore Volume (ml/g) | 1.7 | 1.23 | 1.2 |
| Ratio of pore volume to particle size | 0.014 | 0.003 | 0.020 |
| Oil Adsorption Capacity (g/100 g) | 300 | — | 270-340 |
| Angle of Repose (°) | 36 | 36 | 30 |

Figure 1B:
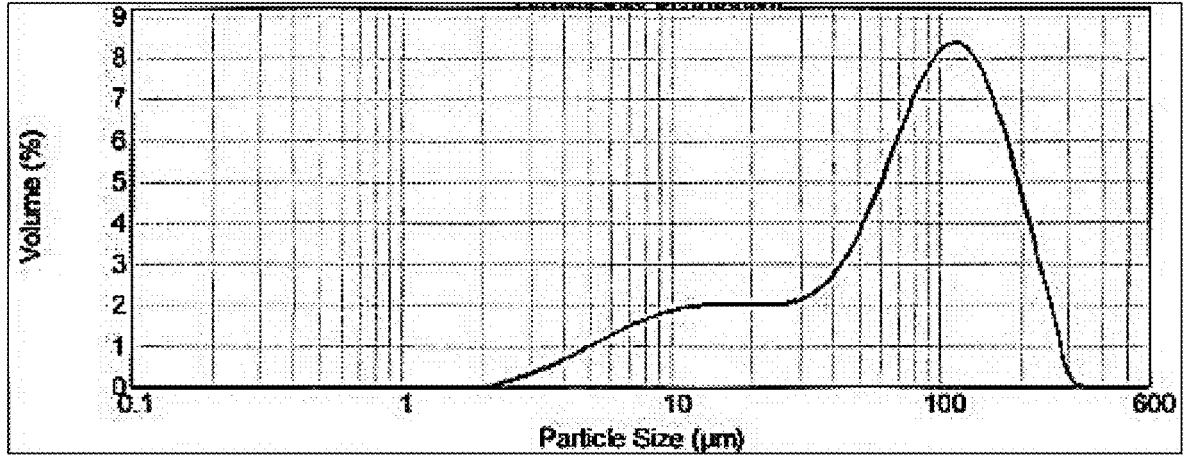
Figure 2A:
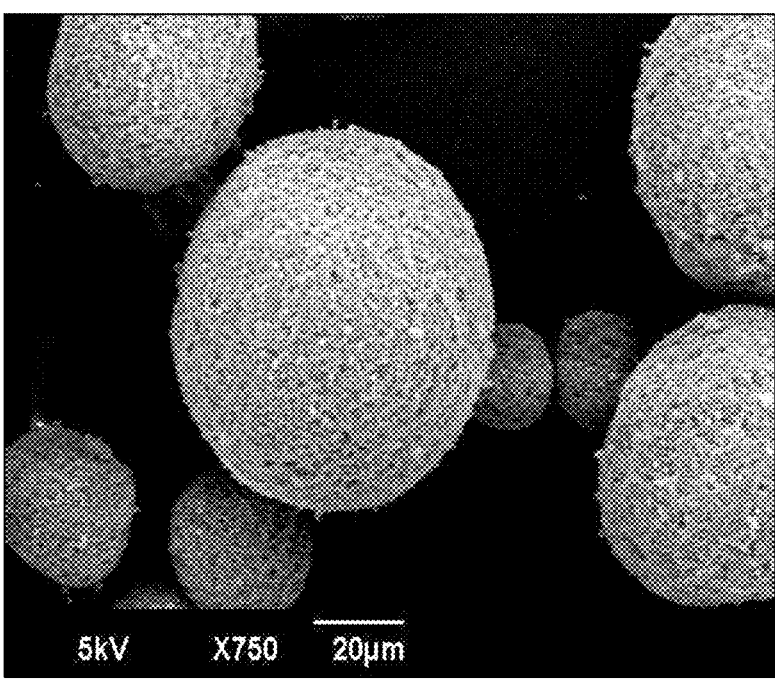
FIGS. 2A and 2B shows scanning electron microscopic (SEM) images of plain Neusilin US2 beads (FIG. 2A) and Neusilin US2 beads loaded with probucol in sesame oil and surfactant (FIG. 2B).
Figure 2B:
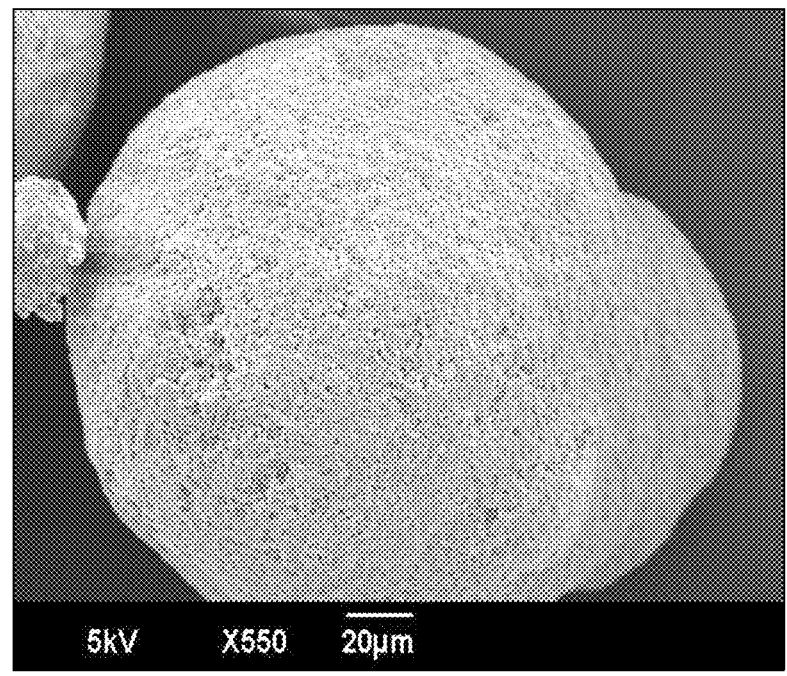

The ratio of pore volume to particle size was determined using dynamic light scattering technique and was highest for Neusilin US2 beads. The particle size distribution for the Neusilin US2 beads is shown in FIG. 1A having d90 as 108 µm and a bimodal distribution. Upon loading of 2:1 ratio of probucol (as a surrogate active ingredient), sesame oil, surfactant, and gel-forming lipid excipient to silica, the particle size distribution of the Neusilin US2 beads was changed to d90 of 182 µm having a unimodal distribution curve, as shown in FIG. 1B. Scanning electron microscopy images for both plain and loaded Neusilin US2 beads are illustrated in FIGS. 2A and 2B. In particular, FIG. 2A depicts plain Neusilin US2 beads and FIG. 2B depicts Neusilin US2 beads loaded with probucol (as a surrogate active ingredient) in sesame oil and a surfactant.

Selection of silica beads considered their flowability upon maximum drug loading. Weight ratios 2:1, 3:1, and 4:1 of probucol (as a surrogate active ingredient) in sesame oil and surfactant to silica were evaluated for the maximum drug loading capacity while retaining the free flowing capacity of the silica beads. Angle of repose of Syloid® XDP 3150 beads and Davisil® LC150A beads is between 35-40° representing passable flowability, as shown in Table 1. However, the angle of repose of Neusilin® US2 beads is 30°, shown in Table 1, which represents better flowability as compared to Syloid® XDP 3150 beads and Davisil® LC150A beads. Upon maximum drug loading, Syloid® XDP 3150 beads and Davisil® LC150A beads displayed a loss in their flowability when loaded with the 2:1 weight ratio of probucol (as a surrogate active ingredient) in sesame oil, surfactant, and gel-forming excipient to silica. Neusilin® US2 beads retained their free flowing properties at the 2:1 and 3:1 weight ratio of probucol (as a surrogate active ingredient) in sesame oil, surfactant, and gel-forming excipient to silica. However, at 4:1 ratio, the flowability of Neusilin® US2 beads appeared to be reduced. Therefore, based on evaluation, Neusilin® US2 beads were identified as a carrier substrate with optimized drug loading of 2:1 and 3:1 weight ratio of probucol (as a surrogate active ingredient) in sesame oil, surfactant, and gel-forming excipient to silica. However, Syloid® XDP 3150 and Davisil® LC150A carrier substrates nonetheless display properties that are conducive for use as the core in the compositions of the present invention.

In embodiments of the invention, one or more surfactants are used in the composition. Surfactants promote self-emulsification. When an emulsion is formed, surface area expansion is created between the two phases. The emulsion is stabilized by the surfactant molecules that form a film around the internal phase droplet. In emulsion formation, the excess surface free energy is dependent on the droplet size and the interfacial tension. If the emulsion is not stabilized using surfactants, the two phases will separate reducing the interfacial tension and the free energy. Self-emulsifying drug delivery systems ("SEDDS") including self-micro-emulsifying drug delivery systems ("SMDDS") are mixtures of natural or synthetic oils, solid or liquid surfactants, or alternatively, one or more hydrophilic solvents and co-solvents/surfactants that have the ability to form oil-in-water emulsions upon mild agitation followed by dilution in aqueous media, such as gastrointestinal fluids. The digestive motility of the stomach and the intestine provides the agitation necessary for self-emulsification.

In the present invention, surfactants may be included to maximize the complete release of the one or more cannabinoids from the pores of the cores. The cannabinoids may be hydrophobic and their release upon dissolution in aqueous medium of the gastrointestinal tract is determined by various intrinsic factors such as fluid volume, peristaltic movement, concentration gradient, food effect, bile salts, and transit time. Since the loading of the one or more cannabinoids onto porous cores is achieved by the capillary action and in consideration of the greater affinity of hydrophobic cannabinoids to the cores, the release of the one or more cannabinoids from the pores warrants an emulsification action.

In some embodiments, the one or more surfactants in the compositions of the present invention may comprise, for example, sorbitan esters, ethoxylated sorbitan esters (Tween® 80; Sigma Aldrich, USA), ethoxylated linear alcohols, ethoxylated alkyl phenols, fatty acid esters, amine and amide derivatives, alkylpolyglucosides, ethyleneoxide/propylene oxide copolymers, polyalcohols and ethoxylated polyalcohols, thiols (e.g., mercaptans) and derivatives, poloxamers, polyethylene glycol-fatty acid esters, lecithins, and mixtures thereof. In certain embodiments, the surfactant may be selected from polysorbates (Tween® 80; Sigma Aldrich, USA), and polyethylene glycol esters of ricinoleic acid (Kolliphor® RH40, Kolliphor® EL; BASF, Germany).

The compositions of the present invention may further comprise one or more stabilizing agents. Examples of stabilizing agents include, but are not limited to, tocopherols, alkyl gallates, butylated hydroxyanisole, butylated hydroxytoluene, ascorbic acid, isoascorbic acid, potassium salt of sulfurous acid (e.g., potassium metabisulfite), sodium salt of sulfurous acid (e.g., sodium met abisulfite), vitamin E, lecithin, ascorbyl palmitate, edetic acid, edetate salt (e.g., EDTA), or a combination thereof. The stabilizing agents may be present in the composition in an amount of about 0.001% to about 5% by weight, or as suitable in order to achieve a stabilized composition.

The composition of the present invention may be in various dosage forms, for example, in capsules, tablets, sachets, sprinkles, or a stick pack. To this end, the composition may further comprise conventional excipients such as diluents, binding agents, fillers, lubricants, disintegrants, or wetting agents.

Examples of diluents include, but are not limited to, cellulose derivatives such as lactose, sucrose, isomalt, cellulose, starch, cyclodextrin, mannitol, microcrystalline cellulose, and sorbitol; calcium carbonate; plain or anhydrous calcium phosphate; calcium hydrogen phosphate dehydrate; calcium phosphate di- or tri- basic; magnesium carbonate; magnesium oxide; starch; sodium chloride; and a combination thereof.

Binders include, but are not limited to, sugars such as sucrose, lactose, and glucose; corn syrup; soy polysaccharide; gelatin; povidone (e.g., Kollidon®, Plasdone®); Pullulan; cellulose derivatives such as microcrystalline cellulose, hydroxypropylmethyl cellulose (e.g., Methocel®), hydroxypropyl cellulose (e.g., Klucel®), ethylcellulose, hydroxyethyl cellulose, carboxymethylcellulose sodium, and methylcellulose; acrylic and methacrylic acid co-polymers; carbomer (e.g., Carbopol®); polyvinylpolypyrrolidine, polyethylene glycol) (Carbowax®); pharmaceutical glaze; alginates such as alginic acid and sodium alginate; gums such as acacia, guar gum, and arabic gums; tragacanth; dextrin and maltodextrin; milk derivatives such as whey; starches such as pregelatinized starch and starch paste; hydrogenated vegetable oil; magnesium aluminum silicate; and a combination thereof.

Fillers may increase the bulk of a dosage form and may make the dosage form easier to handle. Exemplary fillers include, but are not limited to, lactose, dextrose, mannitol, cellulose, starch, and calcium phosphate for solid dosage forms, e.g., tablets and capsules; olive oil and ethyl oleate for soft capsules; water and vegetable oil for liquid dosage forms, e.g., suspensions and emulsions. Additional suitable fillers include, but are not limited to, sucrose, dextrates, dextrin, maltodextrin, microcrystalline cellulose (e.g., PH102 or PH200, Avicel®), microfine cellulose, powdered cellulose, pregelatinized starch (e.g., Starch 1500®), calcium phosphate dihydrate, soy polysaccharide (e.g., Emcosoy®), gelatin, silicon dioxide, calcium sulfate, calcium carbonate, magnesium carbonate, magnesium oxide, sorbitol, kaolin, polymethacrylates (e.g., Eudragit®), potassium chloride, sodium chloride, talc, and combinations thereof. One or more fillers may be used in the dosage form.

Disintegrants can include, but are not limited to, one or more of crospovidone, crystalline cellulose, hydroxypropylcellulose with a low degree of substitution, croscarmellose sodium, carmellose calcium, carboxystarch sodium, carboxymethyl starch sodium, potato starch, wheat starch, com starch, rice starch, partly pregelatinized starch, hydroxypropyl starch, microcrystalline cellulose, alginates, carbonates, and a combination thereof.

Examples of a lubricant can include light anhydrous silicic acid, magnesium stearate, stearic acid, calcium stearate, aluminum stearate, aluminum monostearate, sucrose fatty acid esters, polyethylene glycol, sodium stearyl fumarate, stearyl alcohol, talc, titanium oxide, hydrous silicon dioxide, magnesium silicate, synthetic aluminum silicate, calcium hydrogen phosphate, hardened castor oil, hardened rapeseed oil, Carnauba Wax, bees wax, microcrystalline wax, and sodium lauryl sulfate. One or two or more lubricants may be used.

One or more hydrophilic polymers may be used in a dosage form of the invention. Examples include, but are not limited to, natural or partially or totally synthetic hydrophilic gums such as acacia, gum tragacanth, locust bean gum, guar gum, and karaya gum; cellulose derivatives such as methyl cellulose, hydroxymethyl cellulose, hydroxypropylmethyl cellulose, hydroxypropyl cellulose, hydroxyethyl cellulose, and carboxymethyl cellulose; proteinaceous substances such as agar, pectin, carrageen, and alginates; hydrophilic polymers such as carboxypolymethylene; gelatin;

casein; zein; bentonite; magnesium aluminum silicate; poly-saccharides; modified starch derivatives; and other hydro-philic polymers known in the art. An addition example is a carbomer, such as Carbopol 971P.

Wetting agents may include, but are not limited to, pluronics, polyethylene glycol, sorbitan esters, polysorbates such as polysorbate 20 and polysorbate 80, triton, trometh-amine, lecithin, cholesterol, tyloxapal, and combinations thereof.

In some embodiments, the composition is in the form of tablets or capsules that comprise a coating.

In addition, the composition may comprise one or more natural and/or artificial sweeteners and flavoring agents, or combinations thereof, as known in the art. Examples of sweeteners/flavoring agents may include, but are not limited to, sugar, dextrose, fructose, aspartame, glycerin, mannitol, sucrose, saccharin sodium, acesulfame potassium, dextrates, liquid glucose, maltitol, saccharin, saccharin calcium, sac-charin sodium, sodium cyclamate, sorbitol, stevia, syrup, xylitol, and combinations thereof.

In embodiments of the present invention, the composition of the present invention can exhibit a dissolution profile that is characteristic of extended release. In some embodiments, when subjected to water as a dissolution medium, the composition of the present invention may exhibit a percent release of the one or more cannabinoids of not more than about 20%, or not more than about 30%, or not more than about 40%, or not more than about 50% by weight, after 30 minutes; or not more than about 30%, or not more than about 40%, or not more than about 50%, or not more than about 60% by weight, after 60 minutes; or not more than about 40%, or not more than about 50%, or not more than about 60%, or not more than about 70% by weight, after 120 minutes.

Methods of Preparing the Compositions of the Invention

According to embodiments of the present invention, com-positions comprising one or more cannabinoids according to the present invention may be prepared by mixing the one or more cannabinoids in one or more solubilizers along with one or more gel-forming agents (and in some embodiments one or more surfactants, and optionally one or more stabi-lizing agents) and loading the mixture onto a porous core. The compositions according to these embodiments may be produced by mixing the one or more cannabinoids and the one or more gel-forming agents (and in some embodiments one or more surfactants, and optionally one or more stabi-lizing agents) in one or more solubilizers using, for example, a sonicator and/or a vortex mixer. These components may be mixed in the one or more solubilizers in any order (e.g., first mixing the one or more cannabinoids in the one or more solubilizers and then adding the one or more gel-forming agents and in some embodiments the one or more surfac-tants, or first mixing one or more surfactants in the one or more solubilizers and then adding the one or more cannabi-noids and the one or more gel-forming agents, or adding and mixing each component simultaneously together, etc.). In some embodiments, the one or more cannabinoids and the one or more solubilizers may be mixed with a sonicator until uniform, and then the one or more surfactants (in some embodiments) and the one or more gel-forming agents (and optionally one or more stabilizing agents) may be added and mixed using a vortex mixer. The mixture may then be loaded onto the porous cores by mixing the mixture with the cores. In certain embodiments, a high shear granulator may be used to mix the one or more cannabinoids/one or more gel-forming agents/other components mixture with the porous cores. Thereafter, a composition according to the present invention is formed.

The compositions of the invention may be prepared as capsules, tablets, sachets, sprinkles, or a stick pack, using conventional methodologies.

Methods of Use of the Composition of the Invention

An aspect of the invention relates to methods of treating a health issue in a subject in need thereof, wherein the methods comprise administering an extended release com-position of the invention.

The present invention also relates to the use of an extended release composition of the invention for treating a health issue in a subject in need thereof. The use may comprise administering the composition to the subject.

The present invention relates to the use of an extended release composition of the invention in the manufacture of a medicament for treating a health issue in a subject in need thereof The present invention further relates to an extended release composition of the invention for use in treating a health issue in a subject in need thereof. The use may comprise administering the composition to the subject.

The health issue may be selected from the group consist-ing of pain, nausea, sleep apnea, stress disorders, inflam-mation, depression, anxiety, epilepsy, schizophrenia, migraines, arthritis, weight loss, poor appetite, and a com-bination thereof.

In some embodiments, the composition may be adminis-tered orally.

In some embodiments, prior to administration, the com-position may be sprinkled on food or nutrient that is solid, semi-solid, or liquid; into water; or into other types of liquid drink.

EXAMPLES

Example 1

A study was performed to assess immediate release com-positions (Reference Composition A-C) and extended release compositions (Example Compositions A-C) that comprise different surfactants. This study examined the dissolution profile of the compositions in order to assess the emulsification capacity of each surfactant, and to evaluate the drug-releasing agent in the extended release composi-tions.

The immediate release compositions are particles com-prising a porous silica bead core; a surrogate active ingre-dient, probucol; and a surfactant selected from Tween® 80 (Reference Composition A), Kolliphor® RH40 (Reference Composition B), or Kolliphor® EL (Reference Composition C). Table 2 provides a summary of these compositions, including the quantity of each component. The weight ratio of sesame oil to surfactant was 1:5 in each immediate release composition. To prepare the compositions, the probucol was added to sesame oil in a glass beaker, and a sonicator was used to obtain a uniform mixture. The surfactant was added to the mixture, and a vortex mixer was used to form a homogenous mixture. The mixture was then loaded into pores of the Neusilin® US2 silica beads using a high shear granulator to achieve uniform drug-loaded beads.

TABLE 2

Summary of the components and their quantities
(% w/w) of Reference Compositions A-C.

| Component | Reference Composition A | Reference Composition B | Reference Composition C |
|---|---|---|---|
| Probucol | 1.25% | 1.25% | 1.25% |
| Sesame oil | 11.25% | 11.25% | 11.25% |
| Surfactant | 62.5% | 62.5% | 62.5% |
| | (Tween ® 80) | (Kolliphor ® RH 40) | (Kolliphor ® EL) |
| Neusilin US2 beads | 25% | 25% | 25% |
| TOTAL | 100% | 100% | 100% |

The extended release compositions are particles comprising a porous silica bead core; a surrogate active ingredient, probucol; glyceryl monooleate as a gel-forming agent; and a surfactant selected from Tween® 80 in a weight ratio of 1:1 with the glyceryl monooleate (Example Composition A), Kolliphor® RH40 in a weight ratio of 11.5:1 with the glyceryl monooleate (Example Composition B), and Kolliphor® EL in a weight ratio of about 5.25:1 with the glyceryl monooleate (Example Composition C). Table 3 provides a summary of these compositions, including the quantity of each component. To prepare the compositions, the probucol was added to sesame oil in a glass beaker, and a sonicator was used to obtain a uniform mixture. The surfactant and the glyceryl monooleate were added to the mixture, and a vortex mixer was used to form a homogenous mixture. The mixture was then loaded into pores of the Neusilin® US2 silica beads using a high shear granulator.

TABLE 3

Summary of the components and their quantities
(% w/w) of Example Compositions A-C.

| Component | Example Composition A | Example Composition B | Example Composition C |
|---|---|---|---|
| Probucol | 1.3% | 1.25% | 1.25% |
| Sesame oil | 12% | 11.25% | 11.25% |
| Glyceryl monooleate | 26.7% | 5% | 10% |
| Surfactant | 26.7% | 57.5% | 52.5% |
| | (Tween ® 80) | (Kolliphor ® RH 40) | (Kolliphor ® EL) |
| Neusilin US2 beads | 33.3% | 25% | 25% |
| TOTAL | 100% | 100% | 100% |

A dissolution test was conducted on the compositions using purified water, USP, as the dissolution medium in a dissolution volume of 900 ml. A USP Type II paddle apparatus was used to mix the dissolution medium at a paddle speed of 75 rpm. The bath temperature was 37° C., and a 10-µm porous filter was used to sample aliquots.

Figure 3A:
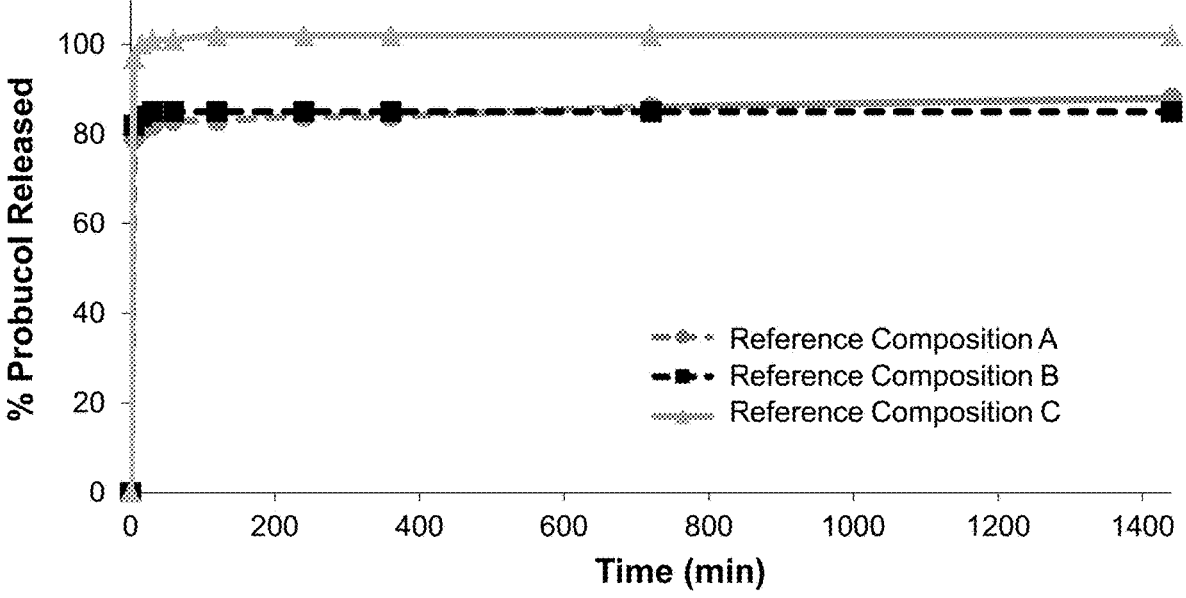
FIGS. 3A and 3B show the dissolution profiles of immediate release Reference Compositions A-C (FIG. 3A) and the dissolution profile of extended release Example Compositions A-C according to embodiments of the invention (FIG. 3B), as described in Example 1.

The dissolution profiles of each immediate release Reference Compositions A-C are provided in Table 4 and in FIG. 3A. Surfactant Tween® 80 was able to facilitate over 80% w/w release of probucol from the Neusilin® in the dissolution medium within 15 minutes as shown in Table 4. Surfactants Kolliphor® RH 40 and Kolliphor® EL were both able to facilitate over 80% w/w release of Probucol in sesame oil from the Neusilin® silica pores in the dissolution medium within 5 minutes, as shown in Table 4.

TABLE 4

Dissolution profile of Reference Compositions A-C.

| Composition | % Drug Release of Probucol | | | | | | | | |
|---|---|---|---|---|---|---|---|---|---|
| | 5 min | 15 min | 30 min | 60 min | 120 min | 240 min | 360 min | 720 min | 1440 min |
| Reference Composition A | 79 | 81 | 82 | 83 | 83 | 84 | 84 | 86 | 88 |
| Reference Composition B | 82 | 84 | 85 | 85 | 85 | 85 | 85 | 85 | 85 |
| Reference Composition C | 100 | 99 | 98 | 98 | 98 | 98 | 99 | 99 | 100 |

FIG. 3A illustrates that all the surfactants evaluated attributed greater than 80% w/w drug release in the dissolution medium. Kolliphor® EL demonstrated the highest emulsification capacity yielding a release after 24 hours of 100% w/w drug from the silica pores as compared to 85% w/w with Kolliphor® RH40 and 88% w/w with Tween® 80.

Figure 3B:
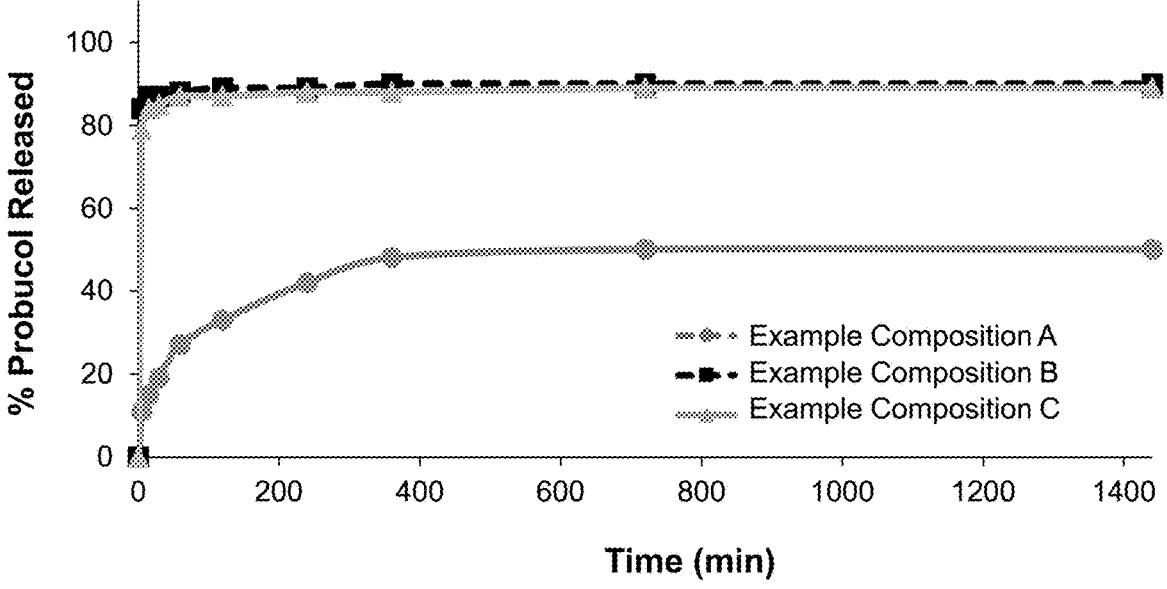

The dissolution profiles of each extended release Example Composition A-C are provided in Table 5 and in FIG. 3B. The dissolution profile of Example Composition A, in which Tween® 80 was used as the surfactant, showed that drug release was extended for the first 6 hours to achieve 50% w/w drug release—and thereby zero order release—for up to 24 hours (see Table 5 and FIG. 3B).

The dissolution profile of Example Composition B, in which Kolliphor® RH40 was used as the surfactant, showed over 80% w/w drug release by 5 minutes (see Table 5 and FIG. 3B). Similarly, the dissolution profile of Example Composition C, which used Kolliphor® EL as the surfactant, showed 79% w/w drug release by 5 minutes and over 80% w/w drug release by 15 minutes (see Table 5 and FIG. 3B).

comprising a porous silica bead core; a surrogate active ingredient, probucol; glyceryl monooleate as a gel-forming agent; and a surfactant Kolliphor® EL at varying ratios with the glyceryl monooleate. Table 6 provides a summary of these compositions, including the quantity of each component To prepare the compositions, the probucol was added to sesame oil in a glass beaker, and a sonicator was used to obtain a uniform mixture. Kolliphor® EL and the glyceryl monooleate were added to the mixture, and a vortex mixer was used to form a homogenous mixture. The mixture was then loaded into pores of the Neusilin® US2 silica beads using a high shear granulator.

A dissolution test was conducted on Example Compositions D-H using purified water, USP, as the dissolution medium in a dissolution volume of 900 ml. A USP Type II paddle apparatus was used to mix the dissolution medium at a paddle speed of 75 rpm. The bath temperature was 37° C., and a 10-μm porous filter was used to sample aliquots.

TABLE 5

Dissolution profile of Example Compositions A-C.

| Composition | 5 min | 15 min | 30 min | 60 min | 120 min | 240 min | 360 min | 720 min | 1440 min |
|---|---|---|---|---|---|---|---|---|---|
| Example Composition A | 11 | 15 | 19 | 27 | 33 | 42 | 48 | 50 | 50 |
| Example Composition B | 84 | 87 | 87 | 88 | 89 | 89 | 90 | 90 | 90 |
| Example Composition C | 79 | 84 | 85 | 87 | 87 | 88 | 88 | 89 | 89 |

These results demonstrate that glyceryl monooleate as a gel-forming agent is capable of providing an extended release profile. In addition, it is hypothesized that the hydrophilicity of glyceryl monooleate may have increased the emulsification action of the beads leading to higher drug release in dissolution medium.

Example 2

Figure 4:
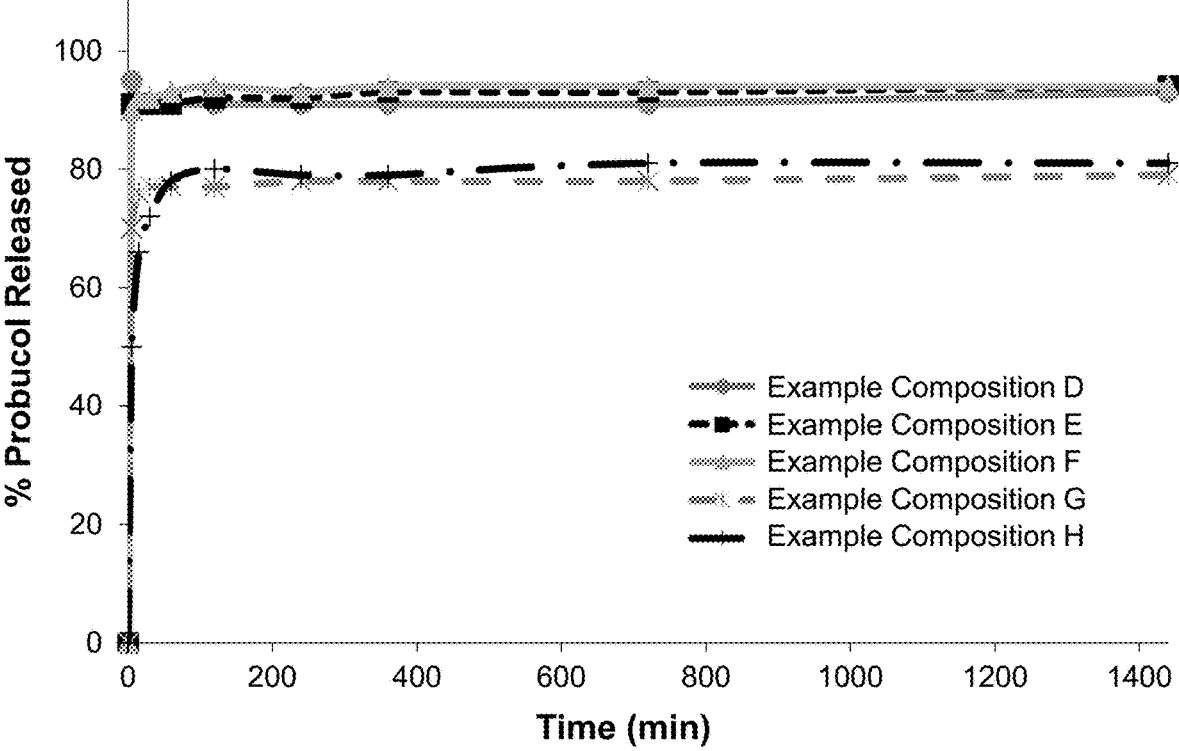
FIG. 4 shows the dissolution profiles of extended release Example Compositions D-H according to embodiments of the invention, as described in Example 2.

A study was performed to assess five extended release compositions (Example Compositions D-H) of particles The dissolution profiles of each composition are provided in Table 7 and FIG. 4. The dissolution profiles of Example Compositions D-F showed that 90% w/w or greater drug release within 5 minutes, which indicates that no extended release was achieved. The dissolution profile of Example Composition G exhibited 70% w/w drug release within 5 minutes, but release remained below 80% w/w through 24 hours. The dissolution profile of Example Composition H showed 50% w/w drug release at 5 minutes, which climbed to 80% w/w by 120 minutes.

TABLE 6

Summary of the components and their quantities (% w/w) of Example Compositions D-H.

| Components | Example Composition D | Example Composition E | Example Composition F | Example Composition G | Example Composition H |
|---|---|---|---|---|---|
| Probucol | 1.2% | 1.1% | 1.1% | 1% | 1% |
| Sesame Oil | 10.7% | 10% | 9.7% | 9.4% | 9% |
| Glyceryl monooleate | 4.7% | 9% | 13% | 16.7% | 20% |
| Kolliphor ® EL | 59.5% | 56.8% | 54.3% | 52.1% | 50% |
| Neusilin US2 beads | 23.8% | 22.7% | 25% | 20.1% | 20% |
| TOTAL | 100% | 100% | 100% | 100% | 100% |

TABLE 7

| | | | | | | | | | |
|---|---|---|---|---|---|---|---|---|---|
| Dissolution profile of Example Compositions D-H. | | | | | | | | | |
| | % Drug Release of Probucol | | | | | | | | |
| Composition | 5 min | 15 min | 30 min | 60 min | 120 min | 240 min | 360 min | 720 min | 1440 min |
| Example Composition D | 95 | 91 | 91 | 91 | 91 | 91 | 91 | 91 | 93 |
| Example Composition E | 91 | 91 | 91 | 91 | 92 | 92 | 93 | 93 | 94 |
| Example Composition F | 90 | 92 | 92 | 93 | 94 | 93 | 94 | 94 | 94 |
| Example Composition G | 70 | 76 | 77 | 77 | 77 | 78 | 78 | 78 | 79 |
| Example Composition H | 50 | 66 | 72 | 78 | 80 | 79 | 79 | 81 | 81 |

These results demonstrate that glyceryl monooleate as a gel-forming agent is capable of providing an extended release profile.

Example 3

A study was performed to compare an immediate release composition (Reference Composition D) and an extended release composition (Example Composition I) of particles comprising a porous silica bead core; cannabinoid THC; and surfactant Tween® 80. The particles of the extended release composition additionally comprises glyceryl monooleate as a gel-forming agent. Table 8 provides a summary of these compositions, including the quantity of each component.

To prepare the immediate release Reference Composition D, the THC was added to sesame oil in a glass beaker, and a sonicator was used to obtain a uniform mixture. The surfactant Tween® 80 was added to the mixture, and a vortex mixer was used to form a homogenous mixture. The mixture was then loaded into pores of the Neusilin® US2 silica beads using a high shear granulator.

To prepare the extended release Example Composition I, the THC was added to sesame oil in a glass beaker, and a sonicator was used to obtain a uniform mixture. The surfactant Tween® 80 and the glyceryl monooleate were added to the mixture, and a vortex mixer was used to form a homogenous mixture. The mixture was then loaded into pores of the Neusilin® US2 silica beads using a high shear granulator.

A dissolution test was conducted on immediate release Reference Composition D and extended release Example Composition I using purified water, USP, as the dissolution medium in a dissolution volume of 900 ml. A USP Type II paddle apparatus was used to mix the dissolution medium at a paddle speed of 75 rpm. The bath temperature was 37° C., and a 10-μm porous filter was used to sample aliquots.

Figure 5A:
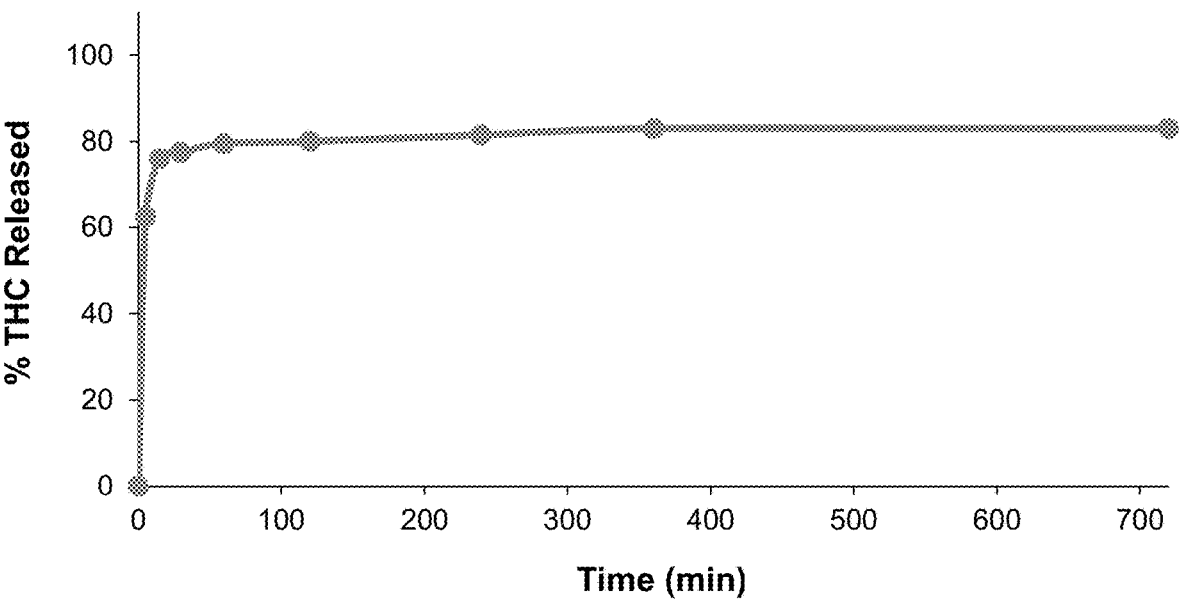
FIGS. 5A and 5B show the dissolution profile of immediate release Reference Composition D (FIG. 5A) and the dissolution profile of extended release Example Composition I according to embodiments of the invention (FIG. 5B), as described in Example 3.
Figure 5B:
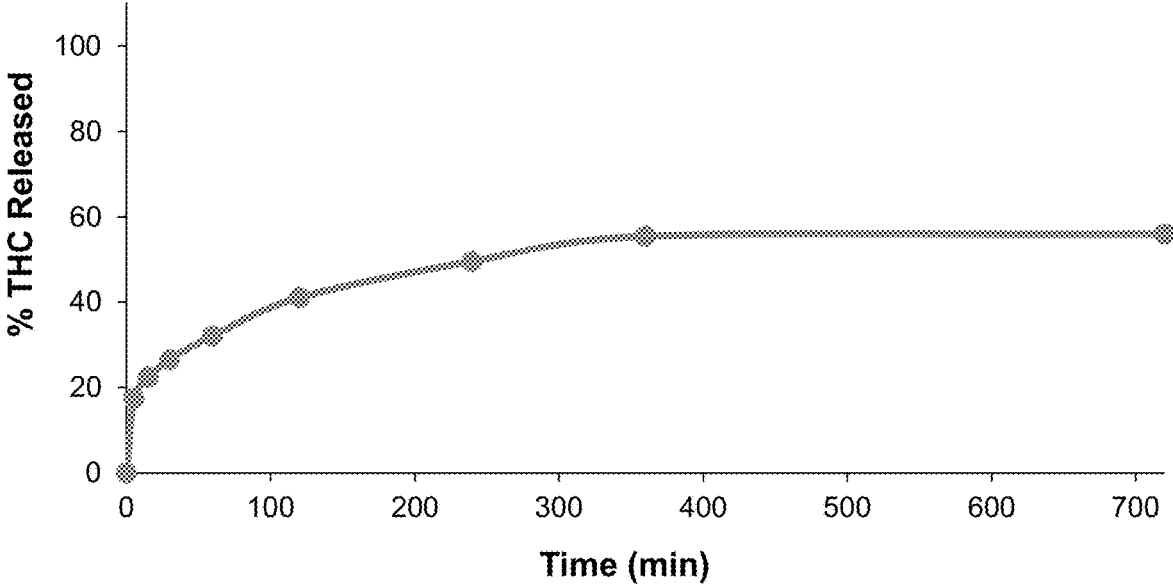

The dissolution profiles of each composition are provided in Table 9 and FIGS. 5A and 5B. The dissolution profile of immediate release Reference Composition D showed 80% w/w THC release after 5 minutes, and about 100% w/w THC release by 12 hours (see Table 9 and FIG. 5A). In contrast, the dissolution profile of extended release Example Composition I showed less than 20% w/w THC release after 5 minutes, and less than 60% w/w drug release after 12 hours (see Table 9 and FIG. 5B).

TABLE 8

| | | |
|---|---|---|
| Summary of the components and their quantities (% w/w) of immediate release Reference Composition D and extended release Example Composition I. | | |
| Component | Immediate Release Reference Composition D | Extended Release Example Composition I |
| THC | 1.4% | 1.4% |
| Sesame oil | 12.6% | 12.6% |
| Surfactant Tween® 80 | 53% | 26.5% |
| Capmul GMO-50 (glyceryl monooleate) | — | 26.5% |
| Neusilin US2 beads | 33% | 33% |
| TOTAL | 100% | 100% |

TABLE 9

| | | | | | | | | |
|---|---|---|---|---|---|---|---|---|
| Dissolution profile of immediate release Reference Composition D and extended release Example Composition I. | | | | | | | | |
| | % Drug Release of THC | | | | | | | |
| Composition | 5 min | 15 min | 30 min | 60 min | 120 min | 240 min | 360 min | 720 min |
| Reference Composition D | 80 | 92 | 93.5 | 95.5 | 96.5 | 98 | 97.5 | 100 |
| Example Composition I | 17.5 | 22.5 | 26.5 | 32 | 41 | 49.5 | 55.5 | 56 |

These results demonstrate that glyceryl monooleate as a gel-forming agent is capable of extending the release of THC.

Example 4

A study was performed to compare an immediate release composition (Reference Composition E) and an extended release composition (Example Composition J) of particles comprising a porous silica bead core; cannabinoid CBD; and surfactant Tween® 80. The particles of the extended release composition additionally comprises glyceryl monooleate as a gel-forming agent. Table 10 provides a summary of these compositions, including the quantity of each component.

To prepare the immediate release Reference Composition E, the CBD was added to sesame oil in a glass beaker, and a sonicator was used to obtain a uniform mixture. The surfactant Tween® 80 was added to the mixture, and a vortex mixer was used to form a homogenous mixture. The mixture was then loaded into pores of the Neusilin® US2 silica beads using a high shear granulator.

To prepare the extended release Example Composition J, the CBD was added to sesame oil in a glass beaker, and a sonicator was used to obtain a uniform mixture. The surfactant Tween® 80 and the glyceryl monooleate were added to the mixture, and a vortex mixer was used to form a homogenous mixture. The mixture was then loaded into pores of the Neusilin® US2 silica beads using a high shear granulator.

A dissolution test was conducted on immediate release Reference Composition E and extended release Example Composition J using purified water, USP, as the dissolution medium in a dissolution volume of 900 ml. A USP Type II paddle apparatus was used to mix the dissolution medium at a paddle speed of 75 rpm. The bath temperature was 37° C., and a 10-μm porous filter was used to sample aliquots.

Figure 6A:
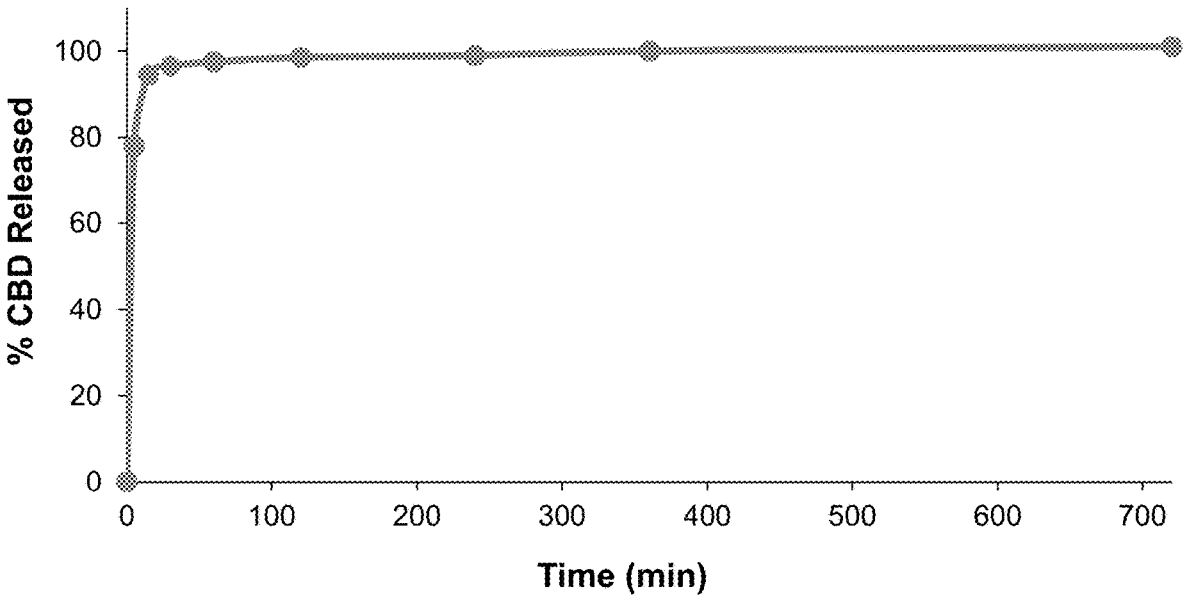
FIGS. 6A and 6B show the dissolution profile of immediate release Reference Composition E (FIG. 6A) and the dissolution profile of extended release Example Composition J according to embodiments of the invention (FIG. 6B), as described in Example 4.
Figure 6B:
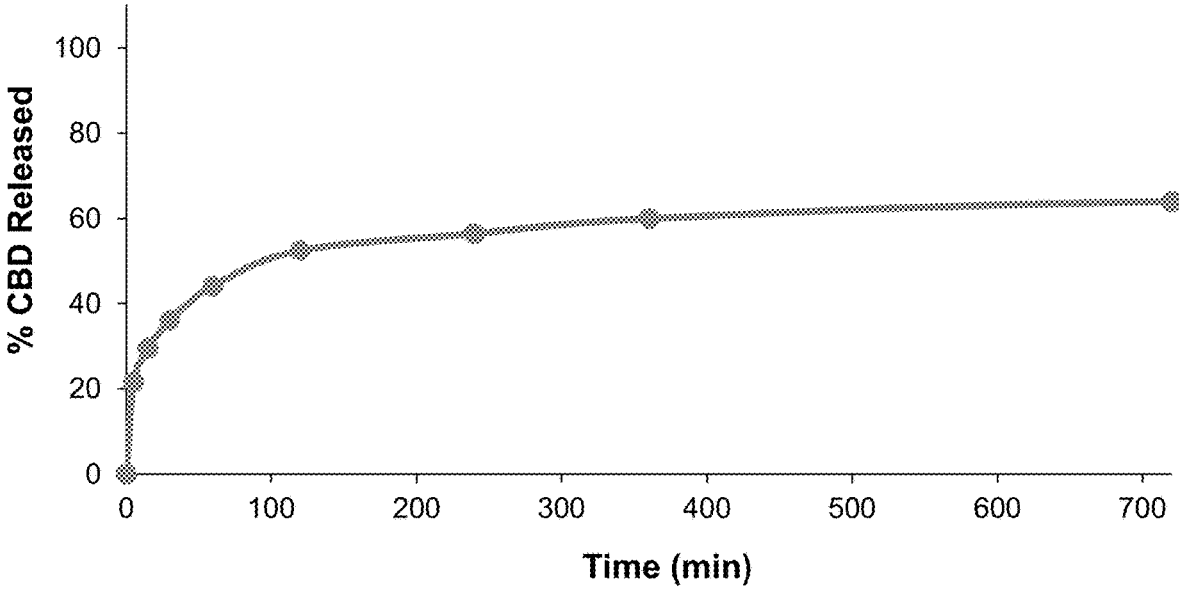

The dissolution profiles of each composition are provided in Table 11 and FIGS. 6A and 6B. The dissolution profile of immediate release Reference Composition E showed over 70% w/w CBD release after 5 minutes, and over 90% w/w CBD release by 15 minutes (see Table 11 and FIG. 6A). In contrast, the dissolution profile of extended release Example Composition J showed less than 25% w/w CBD release after 5 minutes, and less than 70% w/w CBD release after 12 hours (see Table 11 and FIG. 6B).

TABLE 10

Summary of the components and their quantities (% w/w) of immediate release Reference Composition E and extended release Example Composition J.

| Component | Immediate Release Reference Composition E | Extended Release Example Composition J |
|---|---|---|
| CBD | 1.4% | 1.4% |
| Sesame oil | 12.6% | 12.6% |
| Surfactant Tween ® 80 | 53% | 26.5% |
| Capmul GMO-50 (glyceryl monooleate) | — | 26.5% |
| Neusilin US2 beads | 33% | 33% |
| TOTAL | 100% | 100% |

TABLE 11

Dissolution profile of immediate release Reference Composition E and extended release Example Composition J.

| Composition | % Drug Release of CBD | | | | | | | |
|---|---|---|---|---|---|---|---|---|
| | 5 min | 15 min | 30 min | 60 min | 120 min | 240 min | 360 min | 720 min |
| Reference Composition E | 78 | 94.5 | 96.5 | 97.5 | 98.5 | 99 | 100 | 101 |
| Example Composition J | 21.5 | 29.5 | 36 | 44 | 52.5 | 56.5 | 60 | 64 |

These results demonstrate that glyceryl monooleate as a gel-forming agent is capable of extending the release of CBD.

Example 5

A study was performed to compare an immediate release composition (Reference Composition F) and an extended release composition (Example Composition K) of particles comprising a porous silica bead core; cannabinoids THC and CBD; and surfactant Tween® 80 in a capsule. The particles of the extended release composition additionally comprises glyceryl monooleate as a gel-forming agent. Table 12 provides a summary of these compositions, including the quantity of each component.

To prepare the immediate release Reference Composition F, the THC and CBD were added to sesame oil in a glass beaker, and a sonicator was used to obtain a uniform mixture. The surfactant Tween® 80 was added to the mixture, and a vortex mixer was used to form a homogenous mixture. The mixture was then loaded into pores of the Neusilin® US2 silica beads using a high shear granulator, and resulting particles were placed in a capsule.

To prepare the extended release Example Composition K, the THC and CBD were added to sesame oil in a glass beaker, and a sonicator was used to obtain a uniform mixture. The surfactant Tween® 80 and the glyceryl monooleate were added to the mixture, and a vortex mixer was used to form a homogenous mixture. The mixture was then loaded into pores of the Neusilin® US2 silica beads using a high shear granulator, and resulting particles were placed in a capsule.

A dissolution test was conducted on immediate release Reference Composition F and extended release Example Composition K using purified water, USP, as the dissolution medium in a dissolution volume of 900 ml. A USP Type II paddle apparatus was used to mix the dissolution medium at a paddle speed of 75 rpm. The bath temperature was 37° C., and a 10-μm porous filter was used to sample aliquots.

Figure 7A:
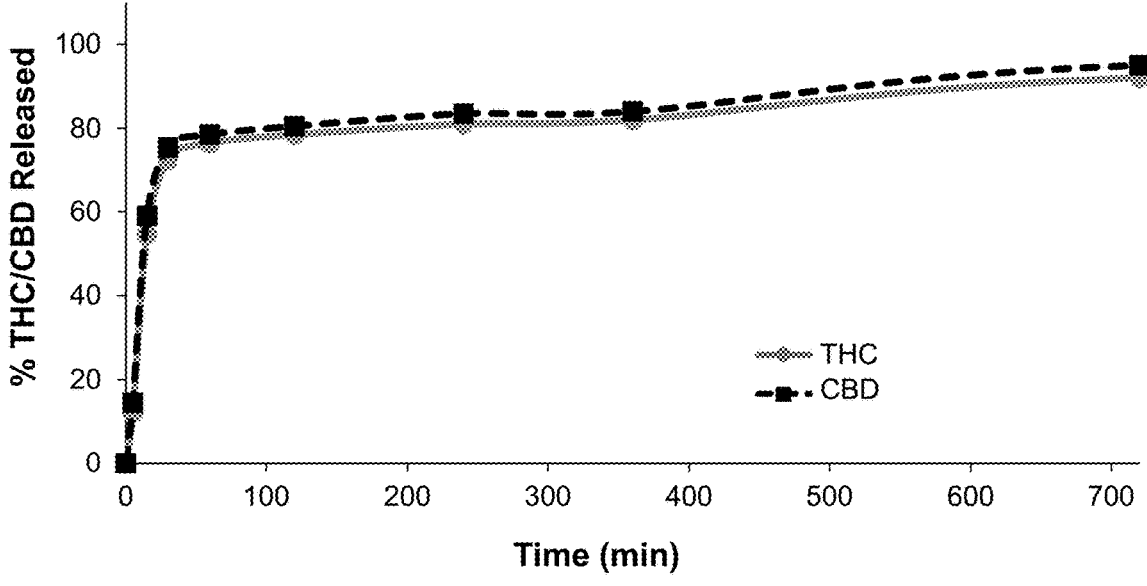
FIGS. 7A and 7B show the dissolution profile of immediate release Reference Composition F (FIG. 7A) and the dissolution profile of extended release Example Composition K according to embodiments of the invention (FIG. 7B), as described in Example 5.
Figure 7B:
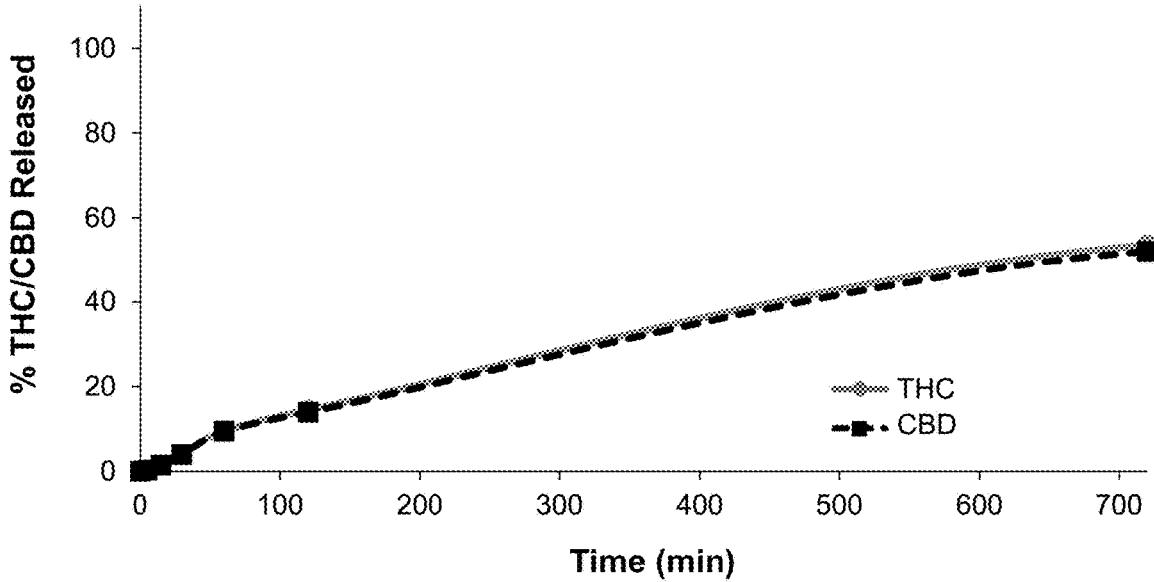
Figures 8A, 8B, 8C:
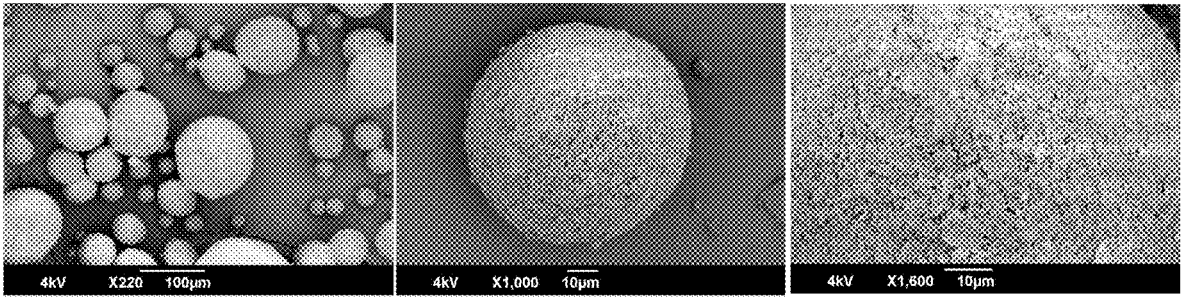
FIGS. 8A-8F shows SEM images of plain Neusilin US2 beads at magnifications of 220× (FIG. 8A), 1000× (FIG. 8B), and 1600× (FIG. 8C); and of Neusilin US2 beads loaded with THC and CBD in sesame oil according to embodiments of the invention at magnifications of 190× (FIG. 8D), 1600× (FIG. 8E), and 2200× (FIG. 8F).
Figures 8D, 8E, 8F:
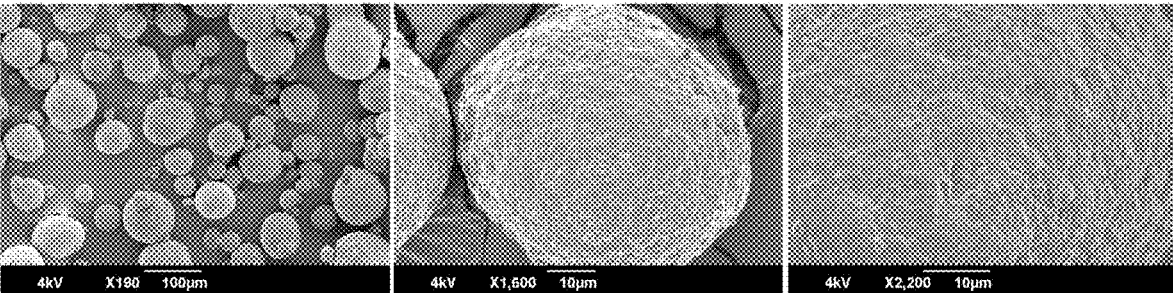

The dissolution profiles of each composition are provided in Table 13 (for release of THC of both compositions) and Table 14 (for release of CBD of both compositions) and in FIG. 7A (release of THC and CBD in immediate release Reference Composition F) and FIG. 7B (release of THC and CBD in extended release Example Composition K). The dissolution profile of immediate release Reference Composition F showed, for both THC and CBD, over 60% w/w release within 30 minutes, and over 90% w/w release by 12 hours (see Tables 13 and 14, and FIG. 7A). In contrast, the dissolution profile of extended release Example Composition K showed, for both THC and CBD, less than 5% w/w release after 30 minutes, and less than 60% w/w release after 12 hours (see Tables 13 and 14, and FIG. 7B).

TABLE 12

Summary of the components and their quantities (% w/w) of immediate release Reference Composition F and extended release Example Composition K.

| Component | Immediate Release Reference Composition F | Extended Release Example Composition K |
|---|---|---|
| THC in sesame oil | 14% | 14% |
| CBD | 1.4% | 1.4% |
| Surfactant Tween ® 80 | 53% | 26.5% |
| Capmul GMO-50 (glyceryl monooleate) | — | 26.5% |
| Neusilin US2 beads | 33% | 33% |
| TOTAL | 100% | 100% |

TABLE 13

Dissolution profile of THC of immediate release Reference
Composition F and extended release Example Composition K.

| | % Drug Release of THC | | | | | | | |
|---|---|---|---|---|---|---|---|---|
| Composition | 5 min | 15 min | 30 min | 60 min | 120 min | 240 min | 360 min | 720 min |
| Reference Composition F | 12 | 54.5 | 72.5 | 76.5 | 78.5 | 81 | 82 | 92 |
| Example Composition K | 0.35 | 1.5 | 4 | 9.5 | 14.5 | | | 53.5 |

TABLE 14

Dissolution profile of CBD of immediate release Reference
Composition F and extended release Example Composition K.

| | % Drug Release of CBD | | | | | | | |
|---|---|---|---|---|---|---|---|---|
| Composition | 5 min | 15 min | 30 min | 60 min | 120 min | 240 min | 360 min | 720 min |
| Reference Composition F | 14.5 | 59 | 75.5 | 78.5 | 80.5 | 83.5 | 84 | 95 |
| Example Composition K | 0.3 | 1.5 | 4 | 9.5 | | | | 52 |

These results demonstrate that glyceryl monooleate as a gel-forming agent is capable of extending the release of THC and CBD.

An analysis was also performed to examine the impact on physical characteristics of loading THC and CBD onto the silica beads. FIGS. 8A-8C and FIGS. 8D-8E compare the physical appearance of plain Neusilin US2 silica beads and of the particles of immediate release Reference Composition F, respectively. The particles loaded with THC and CBD have a more textured surface as compared to the plain Neusilin US2 silica beads.

Figure 9A:
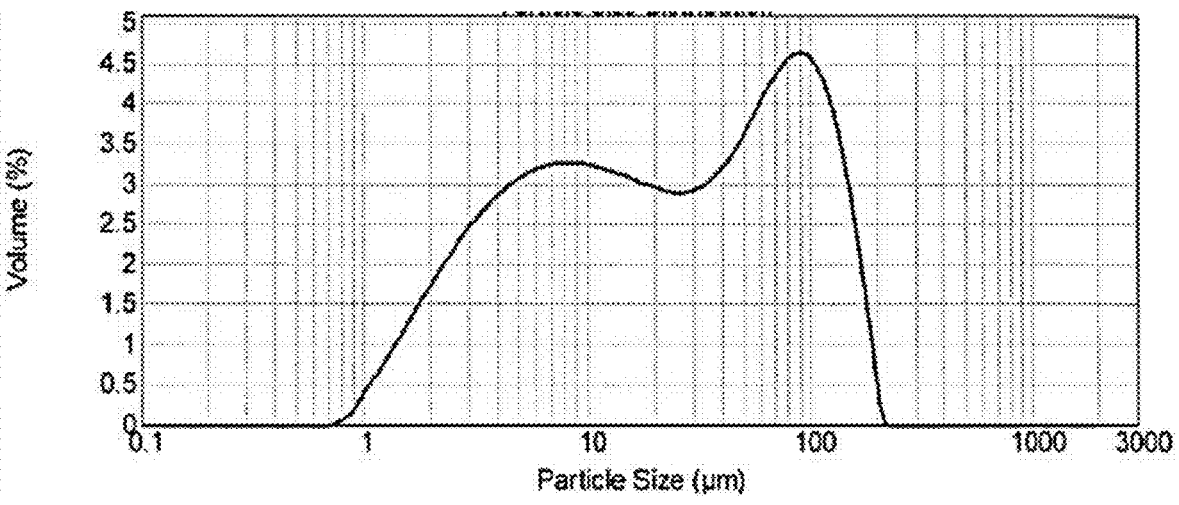
FIGS. 9A and 9B shows particles size distribution profiles of a composition of plain Neusilin US2 beads (FIG. 9A) and a composition of Neusilin US2 beads loaded with THC and CBD in sesame oil according to embodiments of the invention (FIG. 9B).
Figure 9B:
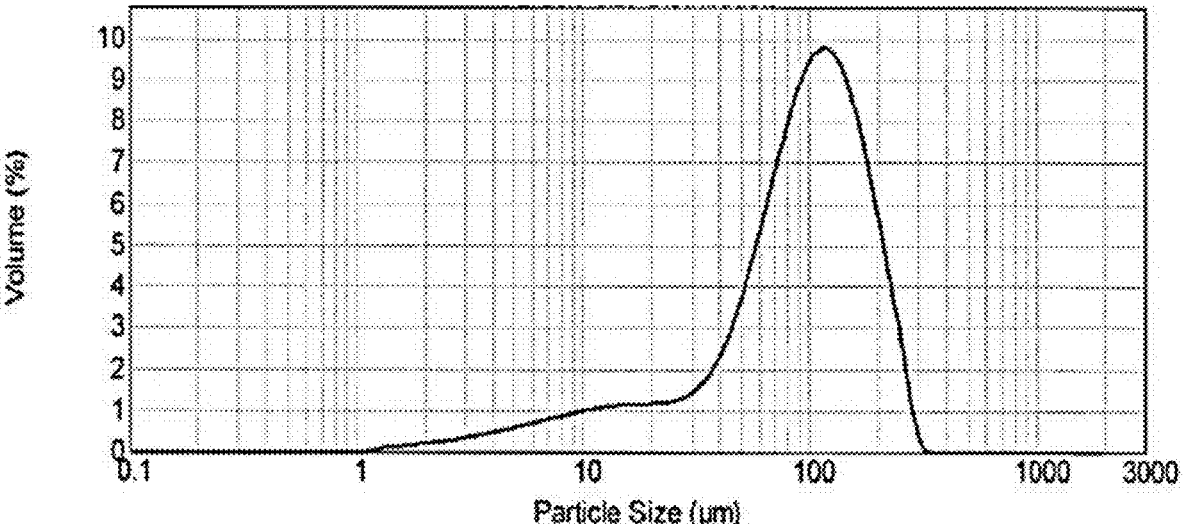

In addition, a comparison of the particle size distribution of the plain Neusilin US2 silica beads and the particles of immediate release Reference Composition F is shown in FIGS. 9A and 9B. The plain Neusilin US2 silica beads exhibited a wider distribution of particle sizes and fewer particles having a diameter of about 40 mm or larger, as compared to the particles of immediate release Reference Composition F (see FIG. 9A compared to FIG. 9B).

Example 6

THC is added in sesame oil in a glass beaker using a sonicator to obtain a uniform mixture. Tween® 80 and the gel-forming agent, glyceryl monooleate, is added to the mixture and mixed homogenously using a vortex mixer. The mixture is loaded into pores of the Neusilin® US2 silica beads using a high shear granulator to achieve uniform drug loaded beads. Tween® 80 is used as a surfactant with glyceryl monooleate in ratio of 1:1. The resultant multiparticulates are loaded into a capsule.

Example 7

CBD is added in sesame oil in a glass beaker using a sonicator to obtain a uniform mixture. Tween® 80 and the gel-forming agent, glyceryl monooleate, is added to the mixture and mixed homogenously using a vortex mixer. The mixture is loaded into pores of the Neusilin® US2 silica beads using a high shear granulator to achieve uniform drug loaded beads. Tween® 80 is used as a surfactant with glyceryl monooleate in ratio of 1:1. The resultant multiparticulate composition is compressed into a tablet.

Example 8

THC and CBD, in combination, are added to sesame oil in a glass beaker using a sonicator to obtain a uniform mixture. Tween® 80 and the gel-forming agent, glyceryl monooleate, are added to the mixture and mixed homogenously using a vortex mixer. The mixture is loaded into pores of the Neusilin® US2 silica beads using a high shear granulator to achieve uniform drug loaded beads. Tween® 80 is used as a surfactant with glyceryl monooleate in ratio of 1:1. The resultant multiparticulates containing CBD and THC are filled into capsules.

Although specific embodiments of the present invention have been disclosed herein, those having ordinary skill in the art will understand that changes can be made to the specific embodiments without departing from the spirit of the invention. The scope of the invention is not to be restricted, therefore, to the specific embodiments. Furthermore, it is intended that the appended claims cover any and all such applications, modifications, and embodiments within the scope of the present invention.

What is claimed is:

1. A composition for extended release of one or more cannabinoids, the composition comprising a population of particles, wherein each particle comprises:

the one or more cannabinoids;

one or more drug-releasing agents which comprise one or more gel-forming agents;

a core; and one or more surfactants;

wherein the composition releases the one or more cannabinoids over a period of at least 6 hours;

wherein the core comprises a calcium carbonate bead or calcium phosphate bead;

wherein the cannabinoids, gel-forming agents, and surfactants form a substantially homogeneous mixture loaded onto the core; and wherein the particles do not comprise a release-mediating layer external to the mixture.

2. The composition of claim 1, wherein the one or more cannabinoids comprises Δ9-tetrahydrocannabinol (THC), cannabidiol (CBD), or a combination thereof.

3. The composition of claim 1, wherein the one or more gel-forming agents is selected from glyceryl monooleate, glycerol monostearate, soybean oil, propylene glycol monopalmitostearate, carboxypolymethylene, hydroxypropyl cellulose, hydroxypropyl methycellulose, carboxymethyl cellulose, chitosan, acacia gum, alginate gums, carrageenan, and guar gum.

4. The composition of claim 3, wherein the one or more gel-forming agents comprises glycerol monooleate.

5. The composition of claim 1, wherein the core comprises one or more pores that extend from the surface of the core.

6. The composition of claim 5, wherein the one or more pores contain the one or more cannabinoids, the one or more drug-releasing agents, and the one or more surfactants.

7. The composition of claim 6, wherein the one or more pores are configured such that the one or more drug-releasing agents is located in the one or more pores closer to the surface of the core than the one or more cannabinoids and the one or more surfactants.

8. The composition of claim 1, wherein the surfactant is selected from the group consisting of sorbitan esters, ethoxylated sorbitan esters, fatty acid esters, polyalcohols, ethoxylated polyalcohols, ethoxylated linear alcohols, ethoxylated alkyl phenols, amine derivatives, amide derivatives, alkylpolyglucosides, ethyleneoxide-propyleneoxide copolymers, thiols, thiol derivatives, poloxamers, polyethylene glycol-fatty acid esters, lecithins, and mixtures thereof.

9. The composition of claim 8, wherein the one or more surfactants is selected from polysorbates and polyethylene glycol esters of ricinoleic acid.

10. The composition of claim 1, wherein the ratio of the one or more surfactants to the one or more drug-releasing agents is about 1:10 to about 10:1 by weight.

11. The composition of claim 10, wherein the ratio of the one or more surfactants to the one or more drug-release agents is about 1:1 by weight.

12. The composition of claim 1, wherein each particle further comprises one or more solubilizers.

13. The composition of claim 12, wherein the one or more solubilizers comprises an oil, glyceride, an alcohol, a hydroalcoholic mixture, or a combination thereof.

14. The composition of claim 12, wherein the ratio of the (one or more cannabinoids+the one or more drug-releasing agents+the one or more surfactants+the one or more solubilizers) to the core is about 2:1 to about 3:1 by weight.

15. The composition of claim 1 wherein the core comprises a calcium carbonate bead.

16. The composition of claim 1 wherein the core comprises a calcium phosphate bead.

17. A composition for extended release of one or more cannabinoids, the composition comprising a population of particles, wherein each particle comprises:

about 1% to about 20% w/w of the one or more cannabinoids;

about 5% to about 15% w/w of one or more solubilizers;

about 15% to about 35% w/w of one or more drug-releasing agents;

about 20% to about 45% w/w of a core; and about 15% to about 35% w/w of at least one surfactant, wherein the composition releases the one or more cannabinoids over a period of at least 6 hours;

wherein the core comprises a calcium carbonate bead or calcium phosphate bead;

wherein the cannabinoids, gel-forming agents, and surfactants form a substantially homogeneous mixture loaded onto the core; and wherein the particles do not comprise a release-mediating layer external to the mixture.

18. The composition of claim 17 wherein the core comprises a calcium carbonate bead.

19. The composition of claim 17 wherein the core comprises a calcium phosphate bead.

20. A method of treating a health issue in a subject in need thereof, comprising administering the composition of claim 1 to the subject, wherein the health issue is selected from the group consisting of pain, nausea, sleep apnea, stress disorders, inflammation, depression, anxiety, epilepsy, schizophrenia, migraines, arthritis, weight loss, poor appetite, and combinations thereof.

21. The method of claim 20, wherein the composition is administered orally.

22. The method of claim 21, wherein prior to administration, the composition is sprinkled on food or nutrient that is solid, semi-solid, or liquid; into water; or into other types of liquid drink.

* * * * *